United States Patent [19]

Crawford et al.

[11] Patent Number: 4,493,329
[45] Date of Patent: Jan. 15, 1985

[54] IMPLANTABLE ELECTRODE HAVING DIFFERENT STIFFENING AND CURVATURE MAINTAINING CHARACTERISTICS ALONG ITS LENGTH

[76] Inventors: Lynn Crawford, 27406 Diane Marie Cir.; William A. McArthur, 27544 Lovage Ct., both of, Saugus, Calif. 91350

[21] Appl. No.: 409,393

[22] Filed: Aug. 19, 1982

[51] Int. Cl.³ .............................................. A61N 1/04
[52] U.S. Cl. ................................. 128/786; 128/419 P
[58] Field of Search .............................. 128/784–786, 128/419 P, 772

[56] References Cited

U.S. PATENT DOCUMENTS

| | | | |
|---|---|---|---|
| 4,020,829 | 5/1977 | Willson et al. | 128/772 X |
| 4,135,518 | 1/1979 | Dutcher | 128/419 P X |
| 4,402,330 | 9/1983 | Lindemans | 128/786 |

*Primary Examiner*—Lee S. Cohen
*Attorney, Agent, or Firm*—John F. Buskirk

[57] ABSTRACT

An implantable stimulation electrode having differing stiffness characteristics along its length. An endocardial electrode (20) is disclosed which includes a spirally-wound, unifilar, continuous portion (50) extending the entire length of the electrode and a stiffening portion (52) which extends for only a portion of the electrode length. The spirals of the stiffening portion (52) and the continuous portion (50) are interleaved in a juxtapositional relationship with respect to each other to form a bifilar section (26), the remainder of the electrode being a unifilar section (28). In the bifilar section (26), each spiral is wound at twice the pitch of the spirals in the unifilar section (28). The bifilar section (26) has a greater stiffness than the unifilar section. In a specific embodiment disclosed, an atrial J electrode is formed in which the bifilar section includes the J portion of the electrode where stiffness is needed. Thus, more flexibility is provided for most of the electrode length where stress concentrations occur, whereas the J portion has additional stiffness for maintaining the electrode in a desired location within the heart atrium (36). A further feature of the disclosed electrode (20) is that the diameter of the bifilar and unifilar sections can be chosen so that the overall electrode has essentially the same diameter as the unifilar section, thus resulting in an electrode having substantially the same cross-sectional profile over its entire length.

11 Claims, 7 Drawing Figures

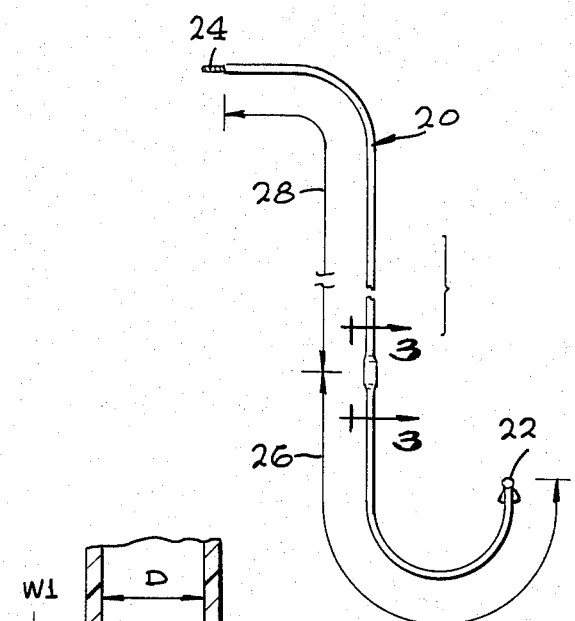
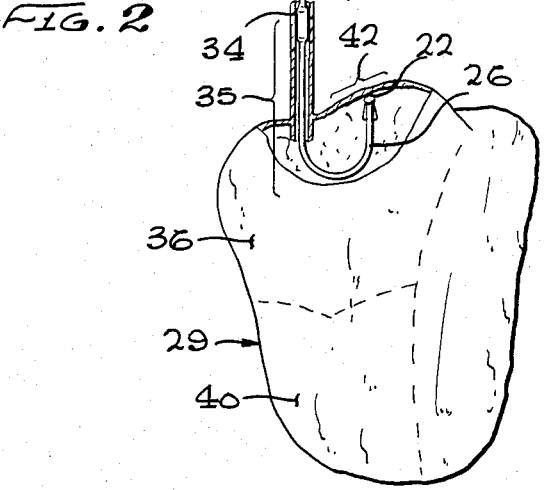
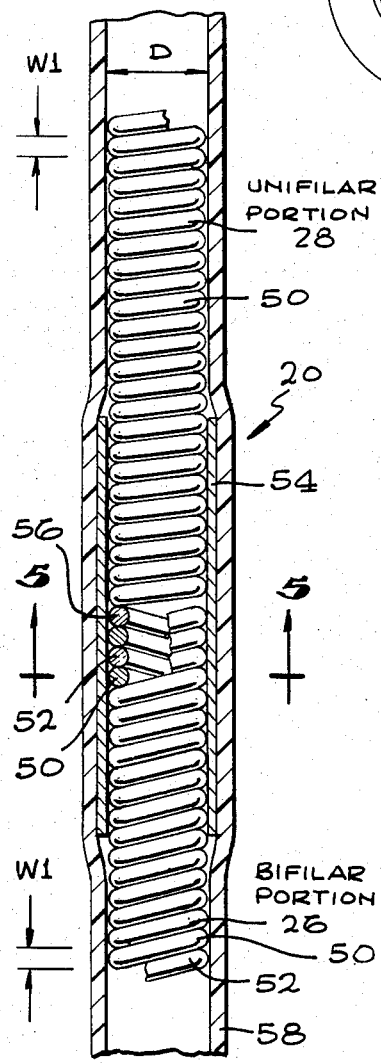
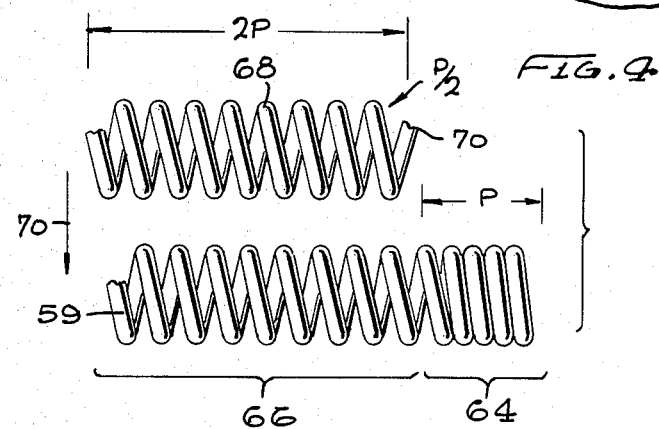
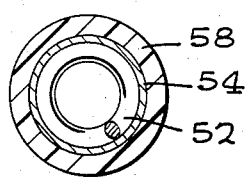
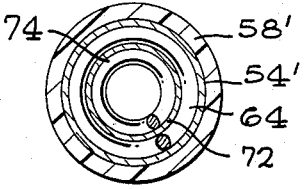
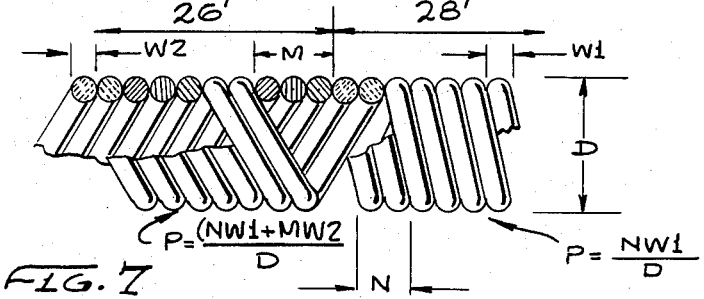

IMPLANTABLE ELECTRODE HAVING DIFFERENT STIFFENING AND CURVATURE MAINTAINING CHARACTERISTICS ALONG ITS LENGTH

FIELD OF THE INVENTION

The invention relates to implantable stimulation electrodes such as endocardial or myocardial electrodes utilized for transmitting electrical impulses from a pulse generator to a predetermined location in a user's body.

BACKGROUND OF THE INVENTION

In conjunction the development of cardiac pacemakers for generating tissue stimulation pulses, endocardial electrodes were developed for transferring stimulation pulses from the pacemaker to the heart. In a typical application, the electrode is inserted into and forced through a vein until the electrode tip enters the heart atrium. Electrodes designed to provide stimulation pulses to the heart wall defining the ventrical chamber are inserted through the heart valve separating the atrium from the ventrical until the electrode tip engages the heart trabeculae within the ventrical. With the advent of pacing within the atrium, a J-shaped electrode was developed so that the electrode tip will be positioned against an upper portion of the atrium, an electrode portion adjacent to the tip being formed in the shape of a "J". It is desirable that this "J" portion have a sufficiently stiff body for ease of insertion and maintenance of the electrode tip in the desired location. However, the stiffness required to maintain the "J" configuration is undesirable in high stress points, such as the upper chest region where the electrode is ligated, stretched, or otherwise highly stressed. Thus electrodes have been developed having greater stiffness in lower stress regions and greater resistance to flexural failure in high stress areas. In order to achieve the greater stiffness, one prior art electrode utilizes coils surrounding the portion of the electrode that needs stiffening. A disadvantage of this approach is that it results in a larger electrode cross-sectional area in the portion where stiffening is required, thereby making veinous insertion of the electrode more difficult. Another prior art electrode utilizes a thicker electrode encasement material over the portion of the electrode to be stiffened. This type electrode also has a larger cross-sectional area for the stiffened portion than for the non-stiffened portion.

SUMMARY OF THE INVENTION

A medical electrode according to the invention solves the above problems by providing an electrode having a substantially constant cross-sectional area throughout its entire length while at the same time having one portion stiffer than another portion. The electrode includes at least one spirally-wound continuous portion of a predetermined length, one end of which is connected to an electrode tip, and at least one spirally-wound stiffening and curvature-maintaining portion having a length less than the predetermined length, the stiffening portion being located in a juxtapositional relationship with respect to a portion of the continuous portion, the continuous portion and stiffening portion combination providing a greater stiffness than the continuous portion alone.

In an exemplary embodiment of the invention, a spirally-wound, unifilar, continuous portion extends the entire length of the electrode, and an additional spirally-wound, unifilar stiffening portion extends for only a portion of the electrode length. The spirals of the stiffening portion and the continuous portion are interleaved in a juxtapositional relationship with respect to each other to form a bifilar section, the remainder of the electrode being defined as a unifilar section. In the bifilar section each spiral is wound at twice the pitch of the spirals in the unifilar section. The transition location between the unifilar and bifilar sections is strengthened by a holding sleeve. The entire lead is encased in a nonconductive material substantially inert to body fluids.

In a further embodiment of the invention, an electrode is disclosed having a continuous portion of N filars, and a stiffening portion of M filars, the relationship between N and M being determined by the desired resistance to flexural failure and stiffness characteristics of the two portions.

BRIEF DESCRIPTION OF THE DRAWINGS

FIG. 1 is a side view of an endocardial electrode provided by the invention;

FIG. 2 is a side view showing the electrode of FIG. 1 connected to a heart pacemaker and having its electrode tip positioned inside the right atrium of a heart.

FIG. 3 is a cross-sectional, partially cut-away side view taken along line 3—3 of FIG. 1;

FIG. 4 is an exploded view showing the stiffening portion of the electrode offset with respect to the continuous portion of the electrode;

FIG. 5 is a cross-sectional view taken along line 5—5 of FIG. 3;

FIG. 6 is a cross-sectional of an electrode configured as a bipolar electrode; and FIG. 7 is a sideview of the interface between the stiffening portion and the continuous portion for a plurality of continuous filars and stiffening filars.

DETAILED DESCRIPTION

Detailed illustrative embodiments of the invention disclosed herein exemplify the invention and are considered to be the best embodiments for such purposes. They are provided by way of illustration and not limitation of the invention. Various modifications thereof will occur to those skilled in the art, and such modifications are within the scope of the claims which define the present invention.

As previously explained, an endocardial electrode is disclosed which provides a first stiffness and flex resistance in a portion adjacent to an exposed electrode tip, and a second stiffness and flex resistance which is different than the first stiffness and flex resistance in the remaining portion of the electrode. In an exemplary embodiment, an atrial J electrode is disclosed with the J portion having greater stiffness and curvature-maintenance than the remainder of the electrode. The electrode itself includes a continuous portion having a single filar of spirally-wound wire. A second spirally-wound stiffening portion also having a single filar is provided, its length being determined by the portion of the electrode to have a greater stiffness. The continuous portion is wound so that each turn of the spirals in the portion to have the lower stiffness has a pitch chosen so that the turns are in an abutting relationship with respect to each other. In the portion of the electrode where greater stiffness is required, the pitch is increased so that the turns of the stiffening portion spirals can be interleaved with the turns of the continuous portion spirals, thereby placing them in a juxtapositional relationship with respect to each other. The electrode thus has substantially the same diameter along its entire length while also having different stiffness characteristics along its length. In a further embodiment of the invention, a plurality of continuous portion filars and a plurality of stiffening portion filars are provided, the specific number being determined by the stiffness required for the various portions of the electrode length.

Referring now to FIGS. 1 and 2, a J-shaped endocardial electrode 20 is shown, the electrode 20 being connected at one end to an electrically-exposed electrode tip 22, the other end 24 being exposed for making electrical contact with an appropriate electrical pulse generator 25. As will be explained in further detail below, a portion of the electrode 20 identified as 26 has greater stiffness and curvature maintenance than the more flexure-resistant portion of the electrode identified as 28. However, as will be further explained below, the diameter of the entire electrode 20 is substantially the same over its entire length.

Referring specifically to FIG. 2, the electrode 20 and electrode tip 22 can be seen positioned in an operative relationship with respect to a user's heart 29. The pulse generator 25 is implanted in a living body, the generator 25 having a receptacle 32 for receiving the other end 24 of the electrode 20. The electrode 20 is inserted through a user's vein 34 so that the J portion 35 enters the right atrium 36 of the heart 29. Providing a stimulation pulse to the atrium 36 as opposed to the ventrical 40 requires a J-shaped portion 35 so that the electrode tip 22 can make electrical contact with a sensitive portion of the atrium 36 as indicated at 42. It is generally appreciated that electrode insertion through the user's vein 34 is facilitated by an electrode having a lower stiffness, whereas the J portion 35 of electrode 20 should have higher stiffness and curvature-maintenance in order to maintain positioning of the tip 22 in the sensitive portion 42 of the atrium 36. As previously explained, prior art electrodes have provided this additional stiffness by utilizing configurations which increase the diameter of the electrode in the portion having the increased stiffness. However, as will be explained below, the exemplary embodiment of the invention provides an electrode having different stiffening and curvature-maintaining characteristics along its length while having a substantially constant cross-sectional area along its length.

A cross-sectional view taken along line 3—3 of FIG. 1 is shown in FIG. 3. Here, the interface between the stiffened portion 26 and the unstiffened portion 28 can be seen. Referring to FIG. 3, a continuous portion 50 includes a single, spirally-wound filar which extends from the electrode tip 22 to the other end 24. The unstiffened portion 28, which is referred to as a unfilar portion, is formed of spirals having a pitch equal to the width W1 of the filar divided by diameter D of the spirals. The stiffened portion 26, which is referred to as the bifilar portion, includes a second single, spirally-wound filar 52 which extends the length of the bifilar portion 26. This portion 52 is referred to as the stiffening and curvature-maintaining portion. The two spirally-wound filars 50 and 52 are interleaved so they are in a juxtapositional relationship with respect to each other. Thus the bifilar portion 26 provides greater stiffness than the unifilar portion 28. In the exemplary embodiment, the width of the second filar 52 is equal to the width W1 of the first filar 50. Thus, the pitch of each spiral in the bifilar portion 26 is equal to twice the width W1 divided by the diameter D. However as can be readily appreciated, different stiffnesses can be obtained by appropriately choosing the width of the second filar 52. A tubularly-shaped sleeve 54 is positioned at the interface between the unifilar portion 28 and the bifilar portion 26 to provide additional support and prevent an end 56 of the second filar 52 from protruding into an encasement tube 58 which is formed of a flexible, non-conductive material that is substantially inert to body fluids. Such a material could be a polyurethane or silicone rubber. The thickness of the sleeve 54 increases the overall diameter of the encasement tube 58 somewhat, thereby resulting in a slight change in the overall diameter of the electrode along its length.

Referring now to FIG. 4, a continuous portion 59 which extends the entire length of the electrode includes a unifilar portion 64 which is wound with a pitch equal to P, P being the width divided by the diameter of each spiral of the conductor as explained in the description associated with FIG. 3. A bifilar portion 66 including a stiffening portion 68 is wound with a pitch equal to 2P, the pitch shown in FIG. 4 being exagerated for purposes of explanation. In an exemplary manufacturing process, the change in pitch between the unifilar and bifilar portions, 64 and 66 respectively, is effected by merely making a pitch setting change in a filar winding machine. The stiffening portion 68 is then located in a coaxial relationship with respect to the continuous portion 59 and manually inserted by screwing the stiffening portion 68 into the continuous portion 59. This interleaves the spiral windings of the stiffening and continuous portions 68 and 59 which have a pitch of 2P, thereby placing them in a juxtapositional relationship with respect to each other. Other manufacturing techniques could also be utilized.

A cross-sectional view of the FIG. 3 electrode taken along line 5—5 is shown in FIG. 5. As can be seen, the center of the electrode is hollow. The sleeve 54 is utilized so that the tip of the stiffening portion 68 as shown in FIG. 4 at 70 will not, through action of the heart, puncture the encasement tube 58. As can be appreciated, the cross-sectional area of the electrode including its encasement tube is constant along its length except for a slightly larger area for the portion of the electrode containing the sleeve 54, thereby resulting in the cross-sectional area only being substantially constant along its entire length. The electrode of FIG. 5 is commonly referred to as a unipolar electrode in which the user's body provides an electrical return path between the electrode tip and the pulse generator which serves as the other electrode.

Another commonly used electrode is a bipolar electrode having two conductors located within the encasement tube, the conductor connected to the electrode tip being of the type previously described, and a return conductor being concentrically located and electrically isolated along its length from the conductor connected to the electrode tip. One end of the return conductor is connected to an annular ring located close to the electrode tip, and in electrical contact with the user's body. Thus, the body only provides a conduction path between the electrode tip and the annular ring. Referring to FIG. 6, a cross-sectional view of a bipolar electrode can be seen. This view would be taken along line 5—5 of FIG. 3 if FIG. 3 had been a bipolar electrode. Included are an encasement tube 58', a tubular-shaped sleeve 54', a unifilar portion 64, a second encasement tube 72, and a return conductor 74. Bipolar leads are well-known in the cardiac pacing field, and need not be described in further detail.

Of course it is not necessary to limit the unstiffened portion 28 or the stiffened portion 26 to one and two filars respectively. More specifically, the unstiffened portion 28 could include a first plurality of filars and the stiffened portion 26 a second plurality of filars. This is illustrated in FIG. 7 where the unstiffened portion 28' could have N filars, the specific number shown in FIG. 7 being two. If the width of each filar is W1, the pitch of each spiral of the unstiffened portion 28' would be NW1 divided by D. The stiffened portion 26' shown in FIG. 7 could also have any number of individual filars greater than those in the unstiffened portion 28', three being the number chosen for illustrative purposes. Assuming that M stiffening filars are utilized, and the diameter of each is W2, then the pitch of each spiral in the stiffened portion 26' would equal (NW1+MW2)/D. Thus using the relationship shown in FIG. 7, any number of filars for the stiffened and unstiffened portions could be chosen to effect a desired absolute and relative stiffness relationship between the two portions.

In the embodiment of the invention shown in FIGS. 1-3, the diameter D of each spiral is 0.039" and the diameter of each filar is 0.010". The sleeve 54 to be located over the transition zone between the unifilar and bifilar portions is a segment of polyurethane tubing having a thickness of 0.007". The encasement tube 58 is formed of high performance silicone rubber having a thickness between 0.010" and 0.015".

We claim:

1. In a medical electrode for conducting an electrical stimulation pulse from a pulse generator to a location within a living body, said electrode being encased in an encasing material which is generally inert to body fluids and terminating in an exposed, electrically conductive electrode tip, an improved electrode comprising:
   at least one spirally-wound continuous portion of a predetermined length one end of which is connected to the electrode tip, said spirals defining a cylinder having a predetermined diameter; and
   at least one spirally-wound stiffening and curvature-maintaining portion having a length less than one half of said predetermined length, said stiffening and curvature-maintaining portion spirals defining a cylinder having substantially the same predetermined diameter as that defined by said continuous portion spirals, the spirals of said stiffening and curvature-maintaining portion being located in a juxtapositional relationship with respect to the spirals of a portion of said continuous portion, said stiffening and curvature-maintaining portion being located within the half of said continuous portion proximal to said electrode tip, said continuous portion and stiffening and curvature-maintaining portion combination providing greater stiffness and curvature maintenance than said continuous portion alone.

2. The improved electrode of claim 1 wherein one end of said stiffening and curvature-maintaining portion is positioned proximal to the electrode tip.

3. The improved electrode of claim 2 wherein said continuous portion and said stiffening and curvature-maintaining portion combination is J-shaped.

4. The improved electrode of claim 2 further comprising a tubularly-shaped sleeve located along said continuous portion and in an overlapping relationship with the other end of said stiffening and curvature-maintaining portion.

5. The improved electrode of claim 1 further comprising:
   at least one return conductor concentrically located within the cylindrical volume defined by said continuous portion; and
   insulating means between said return conductor and said continuous and said stiffening and curvarture-maintaining portions.

6. The improved electrode of claim 1 wherein said at least one spirally-wound continuous portion is one spirally-wound continuous portion and said at least one spirally-wound stiffening and curvature-maintaining portion is one spirally-wound stiffening and curvature-maintaining portion, the diameter of the cylinder defined by said spirally-wound continuous and said spirally-wound stiffening and curvature-maintaining portions is D, the diameter of the spirally-wound continuous portion filar is W1, the diameter of the spirally-wound stiffening and curvature-maintaining portion filar is W2, said electrode being configured so that the pitch of each spiral in said continuous and said stiffening and curvature-maintaining portions is $(W1+W2)/D$ and the pitch of each spiral in said continuous portion alone is $W1/D$.

7. The improved electrode of claim 1 wherein said at least one spirally-wound continuous portion comprises N spirally-wound continuous portions and said at least one spirally-wound stiffening and curvature-maintaining portion comprises M spirally-wound stiffening and curvature-maintaining portions; the sum of N and M being equal to three or more.

8. The improved electrode of claim 7 wherein the diameter of the cylinder defined by said spirally-wound continuous and said spirally-wound stiffening and curvature-maintaining portions is D, the diameter of each spirally-wound continuous portion filar is W1 and the diameter of each spirally-wound stiffening and curvature-maintaining portion filar is W2, said electrode being configured so that the pitch of each spiral in said continuous and said stiffening and curvature-maintaining portions is $(NW1+MW2)/D$ and the pitch of each spiral in said continuous portion alone is $NW1/D$.

9. A medical electrode comprising:
   a longitudinally-extending, spirally-wound continuous portion comprising at least one continuous filar, said spirals defining a cylinder having a predetermined diameter;
   an exposed electrode tip in electrical contact with one end of said continuous portion;
   a longitudinally-extending, spirally-wound stiffening and curvature-maintaining portion comprising at least one continuous filar and having one end adjacent to said electrode tip, said stiffening and curvature-maintaining portion spirals defining a cylinder having substantially the same predetermined diameter as that defined by said continuous portion spirals, the spirals of said stiffening and curvature-maintaining portion being in a juxtapositional relationship with respect to the spirals of said continuous portion, the longitudinal length of said stiffening and curvature-maintaining portion being less than one half of the longitudinal length of said continuous portion; and
   tubular encasement means formed of a substantially body-inert, non-conductive material extending between said electrode tip and the other end of said continuous portion for electrically insulating said continuous portion and said stiffening and curvature-maintaining portion within said tubular encasement means from an external environment.

10. The electrode of claim 9 wherein said continuous portion comprises N longitudinally-extending, spirally-wound, continuous filars in juxtapositional relationship with respect to each other, N being any integer greater than 1.

11. The electrode of claim 9 wherein said stiffening and curvature-maintaining portion comprises M longitudinally-extending, spirally-wound, filars in juxtapositional relationship with respect to each other, M being any integer greater than 1.

* * * * *